(12) United States Patent
Hunt et al.

(10) Patent No.: US 11,020,067 B1
(45) Date of Patent: Jun. 1, 2021

(54) HYDRODYNAMIC BEARING SYSTEM AND METHOD FOR MANUFACTURING THE HYDRODYNAMIC BEARING SYSTEM

(71) Applicant: GE Precision Healthcare LLC, Milwaukee, WI (US)

(72) Inventors: Ian Hunt, Sussex, WI (US); Andrew Triscari, Hubertus, WI (US); John McCabe, Wauwatosa, WI (US); Michael Hebert, Muskego, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 0 days.

(21) Appl. No.: 16/789,302

(22) Filed: Feb. 12, 2020

(51) Int. Cl.
| | |
|---|---|
| H01J 35/10 | (2006.01) |
| A61B 6/03 | (2006.01) |
| G01N 23/04 | (2018.01) |
| F16C 17/10 | (2006.01) |
| F16C 33/10 | (2006.01) |
| G01N 23/046 | (2018.01) |
| A61B 6/00 | (2006.01) |

(52) U.S. Cl.
CPC ............ *A61B 6/032* (2013.01); *A61B 6/4435* (2013.01); *A61B 6/547* (2013.01); *F16C 17/102* (2013.01); *F16C 33/107* (2013.01); *G01N 23/046* (2013.01); *H01J 35/104* (2019.05); *F16C 2316/10* (2013.01); *H01J 2235/106* (2013.01)

(58) Field of Classification Search
None
See application file for complete search history.

(56) References Cited

U.S. PATENT DOCUMENTS

| | | | | |
|---|---|---|---|---|
| 1,816,474 A | * | 7/1931 | Eaton | F16C 23/041 384/286 |
| 4,995,735 A | | 2/1991 | Dansdill | |
| 5,077,775 A | * | 12/1991 | Vetter | F16C 17/107 378/132 |
| 5,602,898 A | * | 2/1997 | Vetter | F16C 17/107 378/132 |
| 5,885,005 A | * | 3/1999 | Nakano | F16C 17/102 315/133 |
| 5,913,608 A | * | 6/1999 | Blume | F16C 17/02 384/192 |

(Continued)

FOREIGN PATENT DOCUMENTS

| | | |
|---|---|---|
| DE | 102015215306 A1 | 2/2017 |
| WO | 2010046837 A2 | 4/2010 |

OTHER PUBLICATIONS

Hattori, H. et al., "Proposal of a High Rigidity and High Speed Rotating Mechanism Using a New Concept Hydrodynamic Bearing in X-Ray Tube for High Speed Computed Tomography," Journal of Advanced Mechanical Design, Systems, and Manufacturing, vol. 3, No. 1, Available as Early as Jan. 2009, 10 pages.

*Primary Examiner* — Thomas R Artman (57) ABSTRACT

Systems and methods related to hydrodynamic bearings are provided. One example system includes a hydrodynamic bearing including a rotational component configured to attach to an anode and a stationary component. The stationary component includes a bearing surface having a plurality of grooves configured to generate pressure in a fluid interface during rotation of the rotational component and where the bearing surface includes at least one recessed section profiled based on an expected pattern of wear.

20 Claims, 5 Drawing Sheets

(56) References Cited

U.S. PATENT DOCUMENTS

| | | | | |
|---|---|---|---|---|
| 6,064,719 | A * | 5/2000 | Vetter | F16C 23/04 |
| | | | | 378/125 |
| 6,082,900 | A * | 7/2000 | Takeuchi | F16C 17/028 |
| | | | | 384/115 |
| 6,123,460 | A * | 9/2000 | Takeuchi | F16C 33/1075 |
| | | | | 384/100 |
| 7,746,982 | B2 * | 6/2010 | Yoshii | H01J 35/101 |
| | | | | 378/133 |
| 8,120,220 | B2 * | 2/2012 | Yamashita | F16C 33/107 |
| | | | | 310/90 |
| 9,599,578 | B2 * | 3/2017 | Yanagita | G01N 23/046 |
| 9,771,978 | B2 * | 9/2017 | Potze | G11B 19/2045 |
| 2006/0140521 | A1 * | 6/2006 | Uenosono | F16C 33/107 |
| | | | | 384/100 |
| 2009/0080616 | A1 * | 3/2009 | Yoshii | H01J 35/101 |
| | | | | 378/133 |
| 2010/0231074 | A1 * | 9/2010 | Yamashita | F16C 33/107 |
| | | | | 310/90 |
| 2011/0280376 | A1 | 11/2011 | Behling et al. | |
| 2017/0102031 | A1 * | 4/2017 | Potze | F16C 33/106 |

* cited by examiner

FIG. 10

HYDRODYNAMIC BEARING SYSTEM AND METHOD FOR MANUFACTURING THE HYDRODYNAMIC BEARING SYSTEM

TECHNICAL FIELD

Embodiments of the subject matter disclosed herein relate to hydrodynamic bearing systems and methods for manufacturing the hydrodynamic bearing systems.

BACKGROUND

Hydrodynamic bearings are used in a various operating environments due to their increased longevity and ability to more effectively manage thermal loads, relative to ball bearings or roller bearings. One such operating environment is the use of hydrodynamic bearings in x-ray tubes of x-ray imaging systems or computed tomography (CT) imaging systems. Certain x-ray tubes, for example, utilize hydrodynamic bearings owing at least in part to their thermodynamic characteristics and durability. However, certain hydrodynamic bearings may experience wear due to loads on the bearings, thermal deformation of bearing components, etc. Hydrodynamic bearings may also be known as liquid metal bearings or spiral groove bearings.

SUMMARY

In one embodiment, a system is provided. The system includes a hydrodynamic bearing having a rotational component configured to attach to an anode and a stationary component. The stationary component includes a bearing surface having a plurality of grooves configured to generate pressure in a fluid interface during rotation of the rotational component. The bearing surface includes at least one recessed section profiled based on an expected pattern of wear.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

The following description relates to various embodiments of hydrodynamic bearing systems. The hydrodynamic bearing systems are designed to reduce wear in a working fluid (e.g., liquid metal) in rotational interfaces of the bearings. To reduce wear in the rotational interface, a recessed section is formed away from pressure generating grooves (e.g., herringbone grooves) in a bearing surface. The recessed section is profiled using an expected wear pattern of the bearing surface during bearing use. For instance, the profile of the recessed section may match the expected wear pattern. In this way, the likelihood of bearing wear caused by rubbing between bearing surfaces in a stationary component (e.g., shaft) and a rotational component (e.g., sleeve) may be reduced. The rubbing in the bearing may be the result of, for example, rotational component shape changes due to the thermal growth of the target and its pull on the rotational component, thermal growth from temperature gradients, joint (e.g., bolted joint) compression, and elasto-hydrodynamics. The bearing wear may also be caused by thermal shape changes to the shaft due to thermal gradients, load pressures, and support structure geometry with reaction forces.

Figure 1:
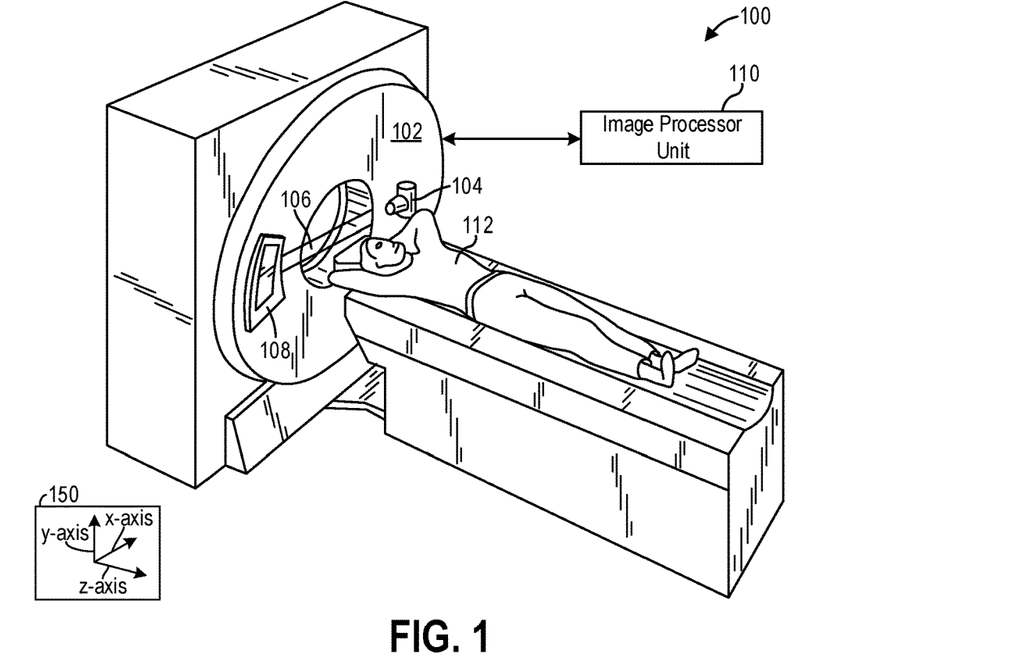
FIG. 1 is a perspective view of an exemplary computed tomography (CT) imaging system.
Figure 2:
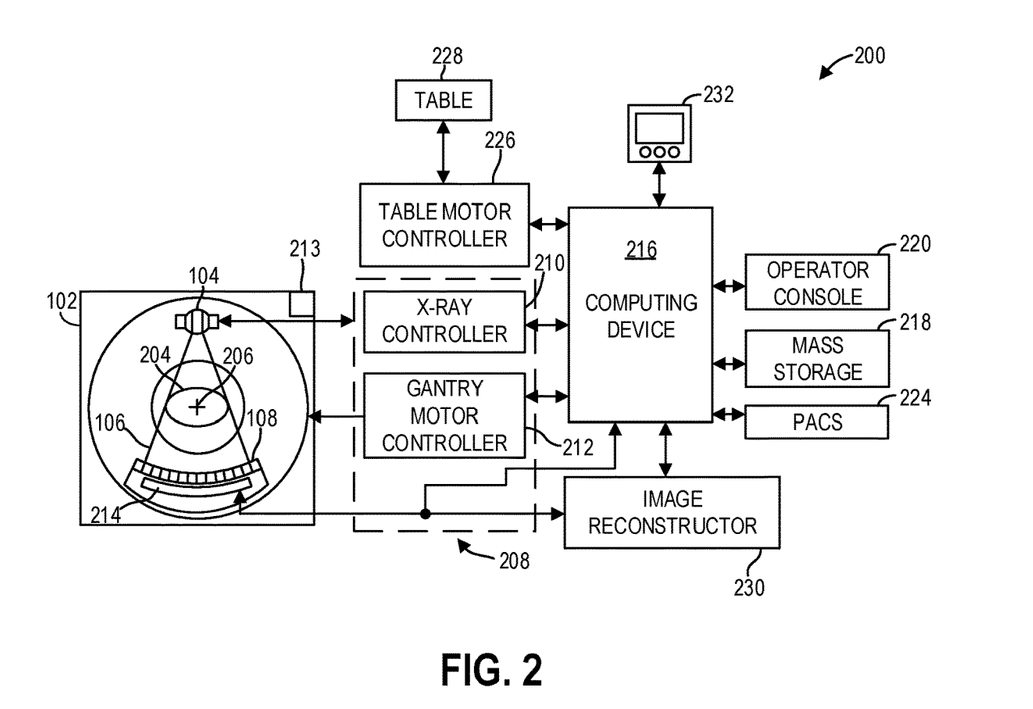
FIG. 2 is a schematic depiction of an exemplary CT imaging system.
Figure 3:
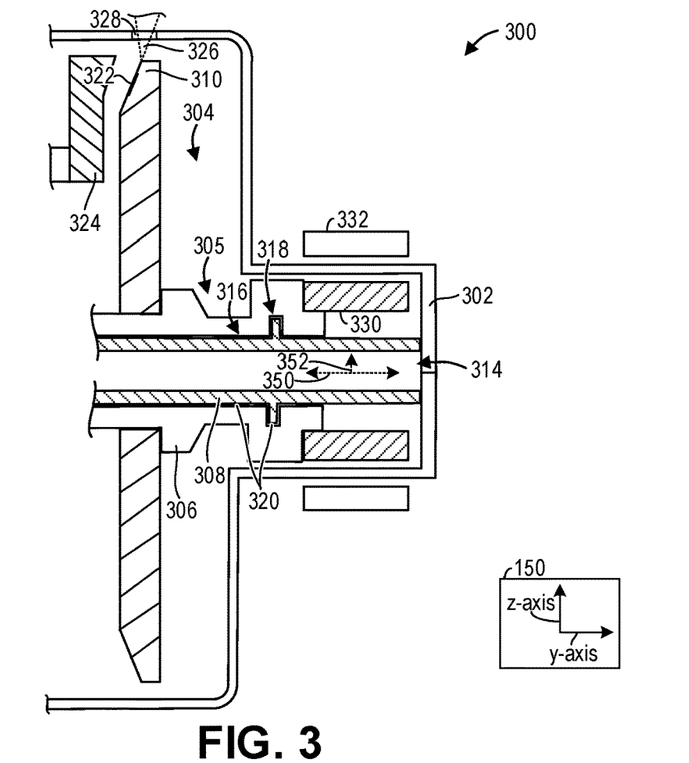
FIG. 3 is a cross-sectional view of an exemplary x-ray source.
Figure 4:
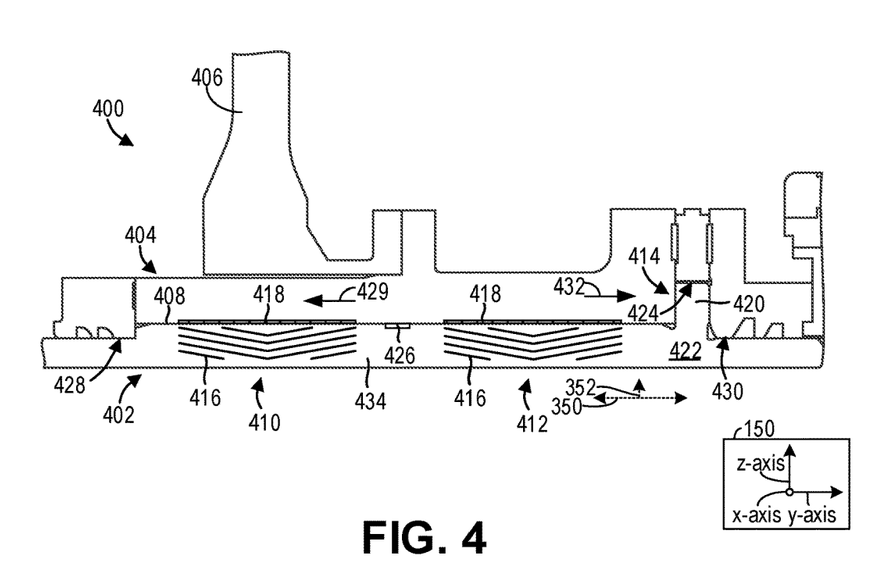
FIG. 4 is a cross-sectional view of a portion of another exemplary x-ray source.
Figure 5:
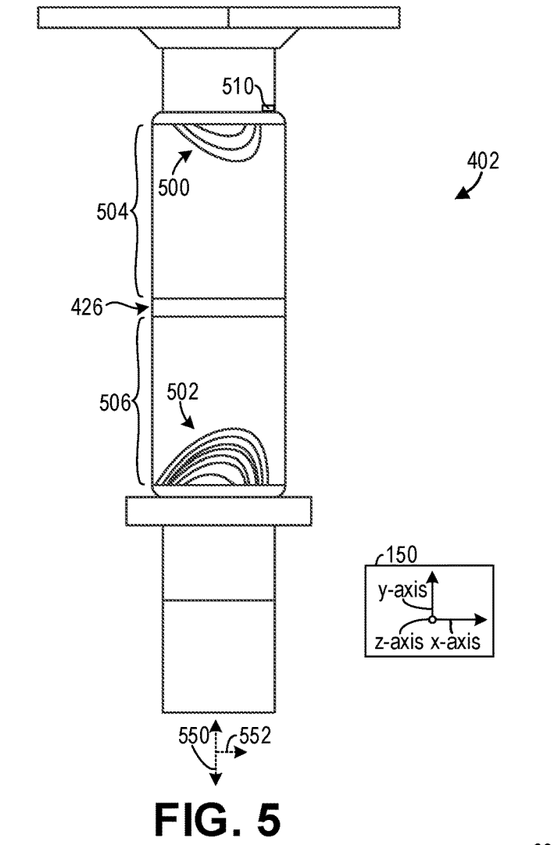
FIG. 5 is a side view of a stationary component in the x-ray source, shown in FIG. 4.
Figure 6:
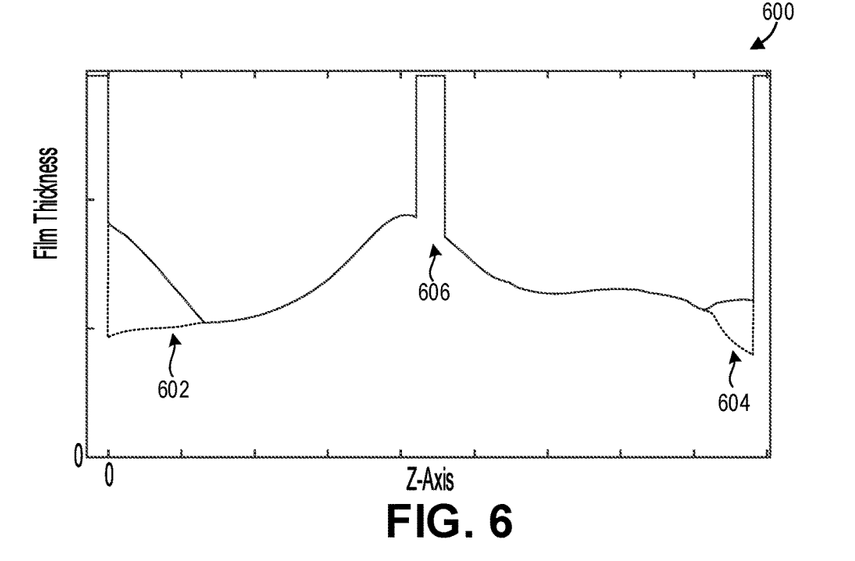
FIG. 6 is a graphical representation of an exemplary expected wear pattern in the stationary component, shown in FIG. 5.
Figure 7:
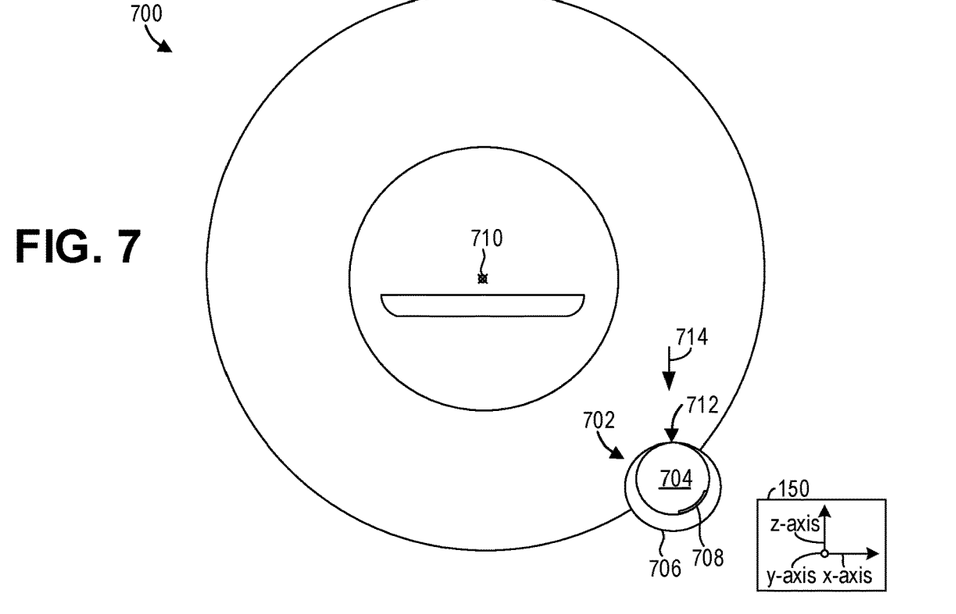
FIGS. 7-8 is an exemplary technique for controlling a gantry having an x-ray source in a CT imaging system.
Figure 8:
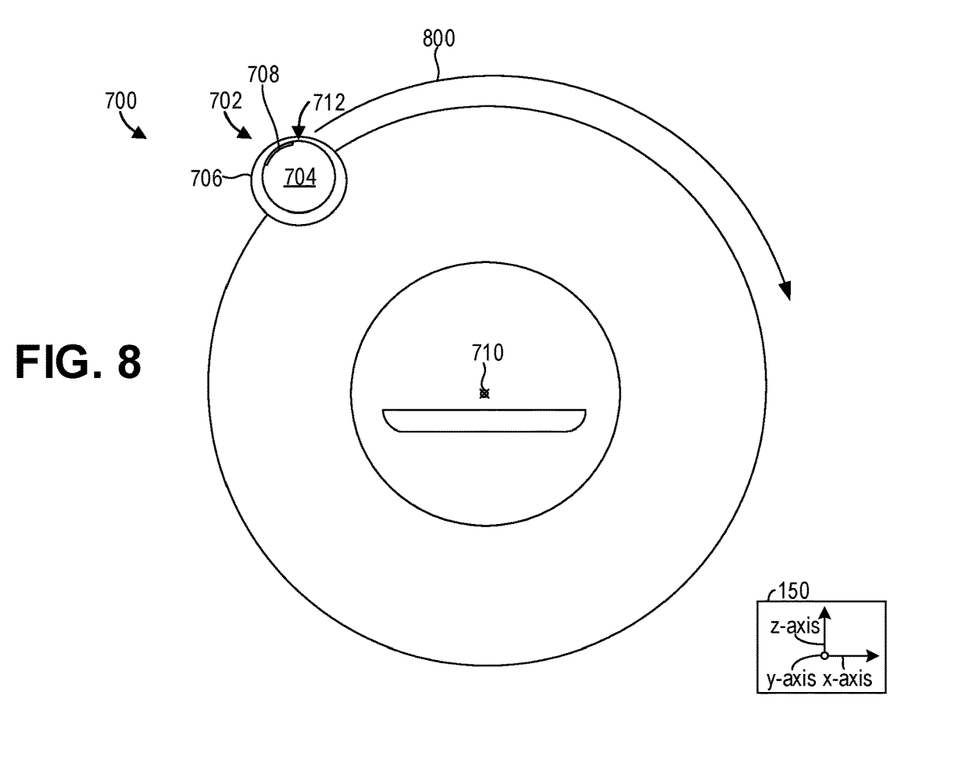
Figure 9:
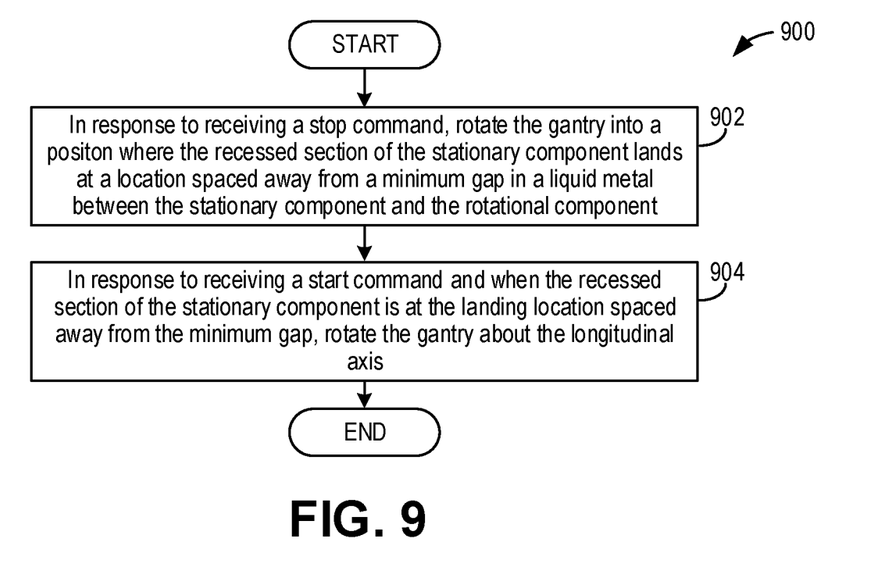
FIG. 9 is a method for operation of a CT imaging system.
Figure 10:
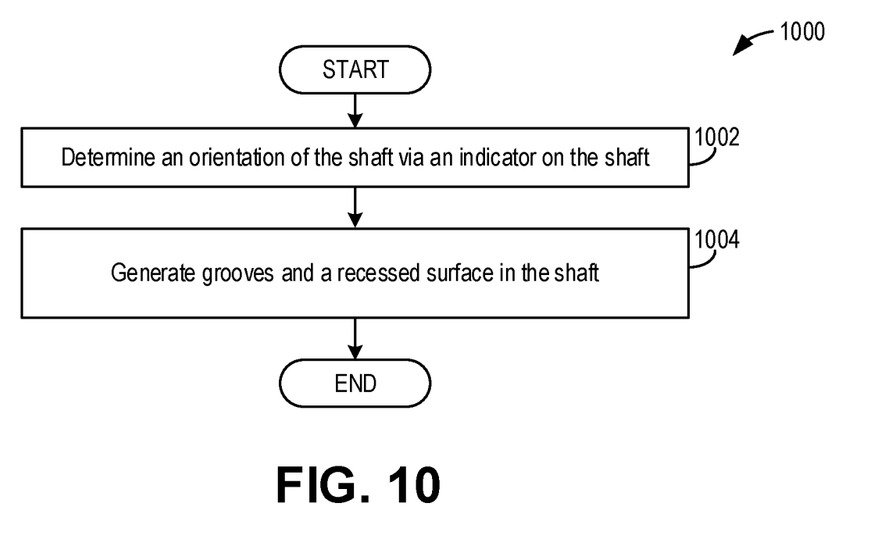
FIG. 10 is a manufacturing method for a hydrodynamic bearing.

FIG. 1 shows an exemplary computed tomography (CT) imaging system with a gantry and FIG. 2 shows another exemplary CT imaging system. FIG. 3 shows a first embodiment of an x-ray source and FIG. 4 shows a second embodiment of an x-ray source. FIG. 5 shows a detailed view of a stationary component in the x-ray source, depicted in FIG. 4. FIG. 6 shows a graphical depiction of an expected wear pattern in a stationary component in a bearing of an x-ray source. FIGS. 7-8 show a control strategy for a gantry in a CT imaging system. FIG. 9 shows a method for operation of a CT imaging system. FIG. 10 shows a method for manufacturing a stationary component in a hydrodynamic bearing.

FIG. 1 illustrates an exemplary CT imaging system 100 configured for CT imaging. Particularly, the CT imaging system 100 is configured to image a subject 112 such as a patient, an inanimate object, one or more manufactured parts, and/or foreign objects such as dental implants, stents, and/or contrast agents present within the body. In one embodiment, the imaging system 100 includes a gantry 102, which in turn, may further include at least one x-ray source 104 configured to project a beam of x-ray radiation 106 for use in imaging the subject 112. Specifically, the x-ray source 104 is configured to project the x-rays 106 towards a detector array 108 positioned on the opposite side of the gantry 102. Although FIG. 1 depicts only a single x-ray source 104, in certain embodiments, multiple x-ray radiation sources and detectors may be employed to project a plurality of x-rays 106 for acquiring projection data at different energy levels corresponding to the patient. Although the x-ray source 104 is shown in a CT imaging system it will be appreciated that the x-ray source may be used in other imaging systems such as radiography imaging systems, fluoroscopy imaging systems, tomography imaging systems, etc.

In some embodiments, the x-ray detector employed is a photon-counting detector which is capable of differentiating x-ray photons of different energies. In other embodiments, two sets of x-ray tube-detectors are used to generate dual-energy projections, with one set at low-kVp and the other at high-kVp. However, numerous suitable x-ray detector configurations have been envisioned.

In certain embodiments, the imaging system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some CT imaging system configurations, a radiation source projects a cone-shaped beam which is collimated to lie within an X-Y-Z plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detector elements are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, e.g., projection data, from the detector array at one gantry angle is referred to as a "view." A "scan" of the object includes a set of views made at different gantry angles, or view angles, during one revolution of the radiation source and detector. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object.

An axis system 150 is provided in FIG. 1 as well as FIGS. 3-5 and 7-8, for reference. The axis system 150 includes a z-axis, a y-axis, and an x-axis. The y-axis may be parallel to a gravitational axis, the z-axis may be a longitudinal axis (e.g., rotational axis of the gantry), and/or the x-axis may be a lateral axis. However, the axes may have other orientations, in other examples.

FIG. 2 illustrates an exemplary CT imaging system 200 similar to the CT imaging system 100 of FIG. 1. In accordance with aspects of the present disclosure, the CT imaging system 200 is configured for imaging a subject 204 (e.g., the subject 112 of FIG. 1). In one embodiment, the CT imaging system 200 includes the detector array 108 (see FIG. 1). The detector array 108 further includes a plurality of detector elements 202 (e.g., detector modules) that together sense the x-ray beams 106 (see FIG. 1) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the CT imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data is commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors. Further in one embodiment, the detector elements 202 may be prismatic detectors or another type of detector with a relatively high energy usage.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT imaging system 200 reveals internal features of the subject 204, expressed in the densities of two basis materials.

In one embodiment, the CT imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements. The gantry 102 may therefore include a motor 213 (e.g., electric motor) designed to rotate the gantry about the center of rotation 206.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive. The DAS 214 may include detector hardware 217 (e.g., readout electronics) configured for detector signal acquisition and processing. For instance, the detector hardware 217 may include analog to digital converters, digital signal processors, amplifiers, etc., designed to process detector signals from the CT detector elements. The DAS 214 may further include one or more local storage devices or mass storage elements to store image data within the DAS for data processing, long term storage, or temporary storage.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the CT imaging system 200, for example, for inputting or outputting system parameters, requesting examinations, plotting data, and/or viewing images. Further, in certain embodiments, the CT imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the CT imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may be a motorized table. Specifically, the table motor controller 226 may move the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the CT imaging system 200 and instead the computing device 216 may perform one or more functions of the image reconstructor 230. Moreover, the image reconstructor 230 may be located locally or remotely, and may be operatively connected to the CT imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

FIG. 3 shows a detailed embodiment of a portion of an x-ray source 300, such as an x-ray source 300. The x-ray source 300 shown in FIG. 3 serves as an example of the x-ray source 104 depicted in FIGS. 1 and 2. As such, the x-ray source shown in FIG. 3 as well as the other x-ray source embodiments described herein may include functional and/or structural features from the x-ray source 104, shown in FIGS. 1 and/or 2, or vice versa. Furthermore, alternate embodiments combining features from one or more of the systems have also been envisioned.

The x-ray 300 includes a housing 302 having a low-pressure enclosure 304 (e.g., vacuum enclosure) formed therein. It will be understood that a low-pressure enclosure infers a comparatively low-pressure relative to atmospheric pressure. As such, the pressure in the enclosure may be less than atmospheric.

The x-ray source 300 includes a hydrodynamic bearing system 305 with a sleeve assembly 306 and a shaft assembly 308. In the illustrated example, the sleeve assembly 306 is a rotational component and the shaft assembly 308 is a stationary component. However, embodiments in which the sleeve assembly is a stationary component and the shaft assembly is a rotational component, have been contemplated. In such an example, an anode 310 may be coupled to the shaft assembly 308 as opposed to the sleeve assembly 306. Nevertheless, in the illustrated embodiment, the anode 310 is coupled to the sleeve assembly 306. It will be understood that the motion denoted by the descriptors stationary and rotating denote the relative motion between the components. However, as previously discussed, the x-ray source may be integrated into a moving structure. For instance, in the CT imaging system use-case, the x-ray source may be integrated into a rotating gantry. As such, in smaller scale frame of reference, the shaft is stationary relative to the sleeve but in a larger scale frame of reference, both components exhibit similar rotational motion in the gantry. However, in alternate use-case scenarios, the x-ray source may be integrated into a stationary structure in regard to the larger scale frame of reference.

The shaft assembly 308 is shown attached (e.g., fixedly coupled) to the housing 302 at a first axial end 314. In some embodiments, the shaft assembly 308, at a second axial end opposing the first axial end 314, may be attached to the housing 302 or other suitable x-ray source component. In this embodiment, the bearing system is formed as a straddle bearing system. However, system embodiments where the shaft assembly 308 is only coupled at one axial end, forming a cantilever arrangement, have been envisioned.

The hydrodynamic bearing system 305 includes a plurality of hydrodynamic bearings including a journal bearing 316 and a thrust bearing 318. The system may however include additional bearings obscured from view in FIG. 3. The journal bearing 316 is designed to support radial loads and the thrust bearing 318 is designed to support axial loads. In this way, loads on the sleeve are managed to enable efficient sleeve rotation.

Each of the bearings include an interface 320 in which a working fluid (e.g., liquid metal) serving as a lubricant and supporting loads. The thickness of the interface may be selected based on factors such as the type liquid metal or other working fluid used in the bearing, manufacturing tolerances of the components, expected system operating temperature, etc. Thus, in one use-case example, the liquid metal interface may be on the order of 5 microns (μm)-40 μm. In one example, the liquid metal used as the working fluid in the bearing assembly may include gallium, tin, indium, combinations thereof, etc. However, working fluid other than liquid metal have been envisioned such grease, oil, combinations thereof, etc.

In the illustrated embodiment, the anode 310 is coupled to the sleeve assembly 306. However, as previously mentioned, embodiments with the anode coupled to rotational shaft assemblies have been envisioned. The anode 310 includes a focal spot 322 serving as a surface receiving a beam of electrons from a cathode 324, during x-ray source 300 operation.

The cathode 324 may receive signals from a controller, such as the x-ray controller 210 shown in FIG. 2, to generate an electron beam directed toward a surface of the anode 310. An x-ray beam 326 is generated when the electron beam from the cathode 324 strikes focal spot 322 of the anode 310. The x-rays are emitted through an x-ray window 328 in the housing 302.

A rotor 330 and a stator 332 are also provided in the x-ray source 300. The rotor 330 is coupled to the sleeve assembly 306, in the illustrated embodiment, and is designed to impart rotational motion thereto. However, in embodiments where the shaft assembly rotates the rotor may be coupled to the first and second shafts in the shaft assembly. The stator 332 is shown positioned external to the low-pressure enclosure 304. However, other suitable stator locations have been envisioned. Typically, the rotor and stator can include windings, magnets, electrical connections, etc., electromagnetically interacting to generate rotor rotation responsive receiving control commands, from for example, the x-ray controller 210, shown in FIG. 2. A rotational axis 350 and a radial axis 352 are provided in FIGS. 3-4 for reference.

FIG. 4 shows another example of a hydrodynamic bearing system 400. It will be appreciated that the bearing system 400, shown in FIG. 4, may be included in the x-ray sources described above with regard to FIGS. 1-3. The hydrodynamic bearing system 400 includes a shaft 402 and a sleeve 404. An anode 406 is shown attached to the sleeve 404. Thus, during system use, the sleeve assembly rotates while the shaft assembly remains relatively stationary. However, as previously mentioned, embodiments where the sleeve assembly is kept stationary and the shaft assembly rotates, have been envisioned.

The hydrodynamic bearing system 400 includes a plurality of bearings. Each of the bearings includes a fluid interface 408 (e.g., liquid metal interface) between a section of the shaft 402 and the sleeve 404. It will be understood that the fluid interfaces circumferentially extend around the shaft 402. The bearings include a first journal bearing 410, a second journal bearing 412, and a thrust bearing 414, in the illustrated embodiment. However, other bearing arrangements for the system such as arrangements with a different amount of journal and/or thrust bearings have been envisioned. The journal bearings support radial loads and the thrust bearing supports axial loads.

The shaft 402 is shown with herringbone grooves 416 associated with the first and second journal bearings 410 and 412. The sleeve 404 may also include grooves (e.g., spiral grooves), schematically depicted at 418. These grooves (e.g., herringbone and spiral grooves) may work in conjunction to generate pressure in the working fluid (e.g., liquid metal) to support the bearing load. It will therefore be understood that the bearings described herein may be self-acting bearings designed to generate pressure using the surface geometries at the bearing interface. However, bearing embodiments with alternate groove patterns or embodiments omitting of at least a portion of the grooves to alter the bearing's flow dynamics, have been contemplated.

The thrust bearing 414 includes a flange 420 radially extending from a body 422 of the shaft 402 toward a complimentary section 424 in the sleeve body. The bearing system 400 may also include a reservoir 426 positioned between the first journal bearing 410 and the second journal bearing 412. The reservoir 426 may be formed as a groove with an annular shape allowing for an additional volume of the working fluid (e.g., the liquid metal) to be maintained in the bearings, if desired.

The hydrodynamic bearing system 400 may further include seals designed to reduce the amount of fluid leaking from the bearings. The seals may be rotating labyrinth seals providing a circuitous path impeding liquid metal flow in axial directions. However, additional or alternate types of suitable seals or combinations of seals have been contemplated such as capillary seals, hydrodynamic seals, flange seals, foil seals, etc. A first seal 428 is shown positioned axially outward (indicated via arrow 429) from the first journal bearing 410. A second seal 430 is shown positioned axially outward (indicated via arrow 432) from the thrust bearing 414.

The surface 434 of the shaft 402 may have recessed sections corresponding to expected or anticipated bearing wear patterns. Shaping the recessed sections with these recessed sections decreasing bearing wear by reducing the likelihood of the shaft and sleeve contacting during bearing rotation due to thermal shape changes of the shaft and/or sleeve, bending of the sleeve caused by relatively high loading, etc. The recessed sections may each exhibit asymmetry about the bearing's rotational axis 350. Further, in some examples, the recessed sections may have local asymmetry with regard to their axial depth profile. Further still, in one use-case example, each of the recessed sections may have circumferential asymmetry but may be arranged in a symmetric pattern axially about the reservoir 426.

FIG. 5 shows a detailed view of the shaft 402 with a first recessed section 500 and a second recessed section 502. As previously mentioned, the recessed sections 500 and 502 may have a depth profile matching an expected wear pattern of the shaft. To elaborate, each of the recessed sections may specifically have circumferential and/or axial asymmetry, allowing the depth of the sections to be granularly tailored to precisely match an expected wear pattern of the shaft 402, in certain cases. A central axis 550 and a radial axis 552 of the shaft 402 are provided for reference. Each of the recessed sections 500 and 502 may have circumferential asymmetry about the central axis 550, in one example. Additionally or alternatively, each of the recessed sections 500 and 502 may have an asymmetric depth profile along the central axis. It will also be understood that the recessed sections 500 and 502 extend inward from the shaft's bearing surfaces.

The expected wear pattern may be calculated using predictive modeling and/or via empirical testing using an x-ray source with the hydrodynamic bearing having a stationary component that does not include the recessed section. In one use-case example, mechanical and thermal load conditions may be created and the rotating speed of the bearing may be reduced until contact was observed between the parts as sensed by accelerometers or motor drive changes, to determine the shaft's expected wear pattern. However, other suitable techniques for determining wear pattern have been envisioned.

The first recessed section 500 is shown positioned on an outer axial side of a first journal bearing section 504, corresponding to the first journal bearing 410 shown in FIG. 4, and the second recessed section 502 is shown positioned on an opposing outer axial side of a second journal bearing section 506, corresponding to the second journal bearing 412 shown in FIG. 4. The reservoir 426 between the first and second journal bearing sections 504, 506 is again illustrated. However, other recessed section locations corresponding to locations where the bearing gaps are expected to close due to thermal deformation, loading, etc., and cause contact (e.g., rubbing) and in some circumstances bearing malfunction, may be used in other examples. For instance, in one use-case example, the recessed sections may be created where fluid films between 0 μm and 6 μm are expected to occur. The shaft 402 may also include a datum, schematically indicated at 510, to allow the orientation of the shaft to be determined during manufacturing, installation, etc.

FIG. 6 illustrates a graphical embodiment 600 of an exemplary expected wear pattern on the shaft 402, shown in FIG. 5. It will be appreciated that the expected wear pattern is provided by way of example.

In the graph the length of the shaft is indicted on the abscissa and fluid film thickness (e.g., liquid metal film thickness) is indicated on the ordinate. The recessed sections of the stationary component corresponding to the expected wear patterns are indicated via dashed lines 602 and 604. It will be appreciated that material is removed from the shaft to form the recessed sections. Various manufacturing techniques for forming the recessed sections may be used such as laser etching, electrochemical machining, grinding, sanding, etc. The manufacturing techniques used to create the recessed sections are discussed in greater detail herein with regard to FIG. 10.

The depth of the reservoir is also indicated at 606. It has been found that forming the recessed sections into the shaft can lead to significant performance improvements. For instance, in one use-case scenario it has been found that by utilizing the recessed sections in the shaft, the bearing may exhibit approximately a 25% performance improvement when compared to bearings that do not account of expected wear caused by sleeve and shaft thermal deformation, sleeve loading, etc. However, it will be understood that the performance gains may vary based on a variety of design factors such as the size of the target, expected operating temperature and speed of the bearing, the type of liquid metal used in the bearing, etc.

FIGS. 7-8 show different control schemes for a gantry 700 which may be included in a CT imaging system. Thus, it will be understood that the gantry 700 may be an example of the gantry 102, shown in FIGS. 1-2. As such, the gantry motor controller 212 and/or the x-ray controller 210, shown in FIG. 2, may send control signals to the gantry 700, shown in FIGS. 7-8, to allow the control schemes to be carried out by the system.

The gantry 700 is shown including a bearing system 702 in an x-ray source. The bearing system 702 includes a stationary component 704 (e.g., shaft) and a rotational component 706 (e.g., sleeve). The stationary component 704 again includes a recessed section 708. It will be understood that the recessed section 708 is asymmetric around a circumference of the stationary component and may have a depth profile corresponding to an expected bearing wear pattern. The control schemes are implemented during stop and start operation in the gantry to reduce bearing wear.

Turning specifically to FIG. 7, showing a control technique for the gantry 700 occurring after a gantry stop command has been received by the gantry controller. Responsive to receiving the stop command, the gantry 700 may be rotated about the longitudinal axis 710 into a landing position (e.g., circumferential location) where the recessed section 708 is spaced away from a minimum gap 712 of a liquid metal or other suitable working fluid in the hydrodynamic bearing. In this way, the landing position of the recessed section 708 during a stop condition may be selected to reduce bearing wear, occurring during a subsequent gantry start. It will be understood that the minimum gap is aligned with a gravitational axis 714.

FIG. 8 shows the gantry 700 being controlled after a start command has been received and after the bearing's recessed section 708 has landed in a desired stop positioned spaced away from the minimum gap 712. As shown in FIG. 8 the bearing system 702 is rotated about the longitudinal axis 710, indicated via arrow 800, and the size of the minimum gap 712 has been increased due to the pressure generated by the grooves in the bearing surfaces during bearing operation.

FIG. 9 shows a method 900 for operation of an imaging system. The method 900 as well as the other control strategies described herein may be implemented by any of the systems, assemblies, components, devices, etc., described above with regard to FIGS. 1-8. However, in other examples, the method 900 may be carried out by other suitable systems, assemblies, components, devices, etc. Instructions for carrying out method 900 and/or the other control strategies described herein may be at least partially executed by a processor based on instructions stored in memory (e.g., non-transitory memory).

At 902, the method includes in response to receiving a stop command, rotating the gantry into a positon where the recessed section of the stationary component lands at a location spaced away from a minimum gap in a liquid metal between the stationary component and the rotational component. For instance, the minimum gap may be located at a top side of the bearing and the recessed section may land near the bottom side of the bearing. However, other suitable landing locations for the bearing's recessed section may be used, in other examples.

Next, at 904 the method includes in response to receiving a start command and when the recessed section of the stationary component is at the landing location spaced away from the minimum gap, rotating the gantry about the longitudinal axis. In this way, gantry rotation may be started up at a location where the recessed section has less of a chance of causing bearing wear. Consequently, the longevity of the bearing is further increased.

FIG. 10 shows a method 1000 for manufacturing a shaft or other stationary component in a hydrodynamic bearing, slated for use in an x-ray source, for example. It will be understood that the method 1000 may be implemented to manufacture the stationary components in any of the bearing systems, described above with regard to FIGS. 1-8. Furthermore, the method 1000 may be carried out via one or more manufacturing devices including a controller and memory. Thus, the device may implement the method responsive to programmatic and/or user commands, for instance.

At 1002, the method includes determining an orientation of the shaft via an indicator on the shaft. For example, a datum on the shaft may be identified to allow for a common frame of reference to be established for the shaft. In one use-case example, the shaft may be coupled to a mandrel designed to spin the shaft. However, other suitable manufacturing devices may be used to manipulate the shaft, in other examples.

Next at 1004, the method includes generating grooves and a recessed section in the shaft. In one example, the grooves and recessed section of the shaft may be manufactured at overlapping time intervals. However, in other examples, the grooves and recessed sections may be manufactured in sequential steps. Further, in one example, the grooves and/or recessed section may be manufactured using laser machining. In such an example, the laser's dwell time and passes may be used to control the contour (e.g., location, depth, etc.) of the recessed section and/or the grooves. In certain circumstances, the laser machining may leave recognizable patterns in the shaft such as uneven ablated pockets of material, which can appear in a matrix like pattern or like weld pool lines. However, in other examples, electrochemical machining, grinding (e.g., lobe grinding), and/or sanding may be used to manufacture the recessed section.

A technical effect of providing a hydrodynamic bearing with a stationary component having a recessed section corresponding to an expected bearing wear pattern is to reduce bearing wear.

In another representation, an x-ray tube is provided with a liquid metal bearing having a circumferentially asymmetric recess whose depth profile substantially matches an expected frictional wear pattern and where the circumferentially asymmetric recesses distinct from a plurality of herringbone grooves configured to generate pressure in a liquid metal interface during x-ray tube operation.

When introducing elements of various embodiments of the present disclosure, the articles "a," "an," and "the" are intended to mean that there are one or more of the elements. The terms "first," "second," and the like, do not denote any order, quantity, or importance, but rather are used to distinguish one element from another. The terms "comprising," "including," and "having" are intended to be inclusive and mean that there may be additional elements other than the listed elements. As the terms "connected to," "coupled to," etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to "one embodiment" or "an embodiment" of the present disclosure are not intended to be interpreted as excluding the existence of additional embodiments that also incorporate the recited features. As described herein "approximately" and "substantially" refer to values of within plus or minus five percent, unless otherwise noted.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A system comprising:
a hydrodynamic bearing including:
   a rotational component configured to attach to an anode;
   a stationary component including:
      a bearing surface having a plurality of grooves configured to generate pressure in a fluid interface during rotation of the rotational component;
   wherein the bearing surface includes at least one recessed section profiled based on an expected pattern of wear, and
   wherein the at least one recessed section comprises a portion of the circumference of the stationary component that is less than the full circumference.

2. The system of claim 1, where the geometry of the at least one recessed section corresponds to a wear pattern in the stationary component anticipated to occur during system operation.

3. The system of claim 1, where the at least one recessed section is asymmetric around a circumference of the stationary component.

4. The system of claim 1, where the at least one recessed section is laser etched.

5. The system of claim 1, where the hydrodynamic bearing is a journal bearing.

6. The system of claim 1, where the plurality of grooves are herringbone grooves.

7. The system of claim 1, where the hydrodynamic bearing is a liquid metal bearing.

8. The system of claim 1, where the hydrodynamic bearing is a straddle bearing and where the stationary component is fixedly attached to a housing at opposing axial ends.

9. The system of claim 1, further comprising:
a gantry configured to rotate about a longitudinal axis and including an x-ray tube with the hydrodynamic bearing, where the system further includes:
memory storing instructions; and
a processor electronically coupled to the memory and when executing the instructions is configured to:

responsive to receiving a stop command, rotate the gantry into a position where the at least one recessed section of the stationary component lands at a location spaced away from a minimum gap in a liquid metal between the stationary component and the rotational component.

10. The system of claim 9, further comprising:
memory storing instructions; and
where the processor is electronically coupled to the memory and when executing the instructions is configured to:
responsive to receiving a start command and when the stationary component is at the landing location spaced away from the minimum gap, rotate the gantry about the longitudinal axis.

11. The system of claim 1, where the hydrodynamic bearing is a journal bearing and where the at least one recessed section is spaced away from a thrust bearing.

12. A method for manufacturing a liquid metal bearing comprising:
forming a recessed section in a stationary component of the liquid metal bearing corresponding to a wear pattern in the stationary component expected to occur during liquid metal bearing operation;
where the stationary components includes a bearing surface having a plurality of grooves configured to generate pressure in a liquid metal interface during rotation of the rotational component, and wherein the at least one recessed section comprises a portion of the circumference of the stationary component that is less than the full circumference.

13. The method of claim 12, where the recessed section is asymmetric around a circumference of the stationary component.

14. The method of claim 12, where the step of forming the recessed section includes laser etching the recessed section.

15. The method of claim 12, where the plurality of grooves are herringbone grooves.

16. A computed tomography (CT) imaging system comprising:
an x-ray source with a journal liquid metal bearing including:
a sleeve configured to attach to an anode; and
a shaft including:
a bearing surface having a plurality of grooves configured to generate pressure in a liquid metal interface during rotation of the sleeve;
a recessed section spaced away from the bearing surface and profiled to substantially match an expected pattern of wear, and
wherein the at least one recessed section comprises a portion of the circumference of the stationary component that is less than the full circumference.

17. The CT imaging system of claim 16, further comprising:
a gantry configured to rotate about a longitudinal axis and including an x-ray tube with the liquid metal bearing;
memory storing instructions; and
a processor electronically coupled to the memory and when executing the instructions is configured to:
responsive to receiving a stop command, rotate the gantry into a position where the recessed section of the shaft lands at a location spaced away from a minimum gap in a liquid metal between the shaft and the sleeve; and
responsive to receiving a start command and when the shaft is at the landing location spaced away from the minimum gap, rotate the gantry about the longitudinal axis.

18. The CT imaging system of claim 16, where the recessed section is asymmetric around a circumference of the shaft.

19. The CT imaging system of claim 16, where the recessed section is laser etched.

20. The CT imaging system of claim 16, where the liquid metal bearing is a journal bearing and where the plurality of grooves are herringbone grooves.

* * * * *